United States Patent [19]
Fukui et al.

[11] Patent Number: 5,047,214
[45] Date of Patent: Sep. 10, 1991

[54] SMELL SENSING ELEMENT AND SMELL SENSING DEVICE

[75] Inventors: Kiyoshi Fukui, Osaka; Tesshi Shigemori, Nishinomiya; Katsuo Ehara, Tokyo, all of Japan

[73] Assignee: New Cosmos Electric Co., Ltd., Osaka, Japan

[21] Appl. No.: 320,602

[22] Filed: Mar. 8, 1989

[51] Int. Cl.⁵ .............................. G01N 27/12
[52] U.S. Cl. ...................... 422/98; 422/96; 422/88; 73/31.06; 338/34
[58] Field of Search ............. 422/97, 83, 88, 98, 422/96, 94, 90; 73/23.34, 31.06; 338/34; 340/634

[56] References Cited
U.S. PATENT DOCUMENTS

| | | | |
|---|---|---|---|
| 4,535,315 | 8/1985 | Sakai | 73/31.06 |
| 4,770,027 | 9/1988 | Ehara et al. | 73/23.34 |
| 4,849,180 | 7/1989 | Fukui | 338/34 |

FOREIGN PATENT DOCUMENTS

| | | | |
|---|---|---|---|
| 54-114296 | 9/1979 | Japan. | |
| 1083142 | 3/1989 | Japan | 422/98 |

*Primary Examiner*—Robert J. Warden
*Assistant Examiner*—Howard Hampel
*Attorney, Agent, or Firm*—Jones, Tullar & Cooper

[57] ABSTRACT

A smell sensing element and a smell sensing device utilizing the element. The smell sensing element has a semiconductor portion formed mainly of $SnO_2$. The semiconductor portion has a first component of at least one selected from the group consisting of oxides of alkaline earth metals and a second component of at least one selected from the group consisting of oxides of Sc, Y, Ti, Zr, Hf, Th, Al, Ga and lanthanoids added thereto.

11 Claims, 3 Drawing Sheets

SMELL SENSING ELEMENT AND SMELL SENSING DEVICE

BACKGROUND OF THE INVENTION

1. Field of the Invention

The present invention relates to a smell sensing element and a smell sensing device using the element.

2. Description of the Prior Art

It is known to evaluate smell or odor by human olfactories, by a gas chromatograph or by a gas sensor constituted by use of such a metal oxide semiconductor as $SnO_2$ (Japanese patent laid-open under No. 54-114296).

However, the first method using the human olfactories has the disadvantages of troublesome evaluation procedures and of difficult and expertise-requiring evaluation. The second method using gas chromatograph has the disadvantages of its great size and its unsuitability for portable use and its incapability of speedy real-time analysis. On the other hand, by the third method using a metal oxide semiconductor as the sensing element, the device may be miniaturized for portable use. However, the device needs some improvements in its sensitivity and precision and the same has been incapable of providing precise evaluation.

SUMMARY OF THE INVENTION

The primary object of the present invention is to overcome the above-noted shortcomings of the prior art and to provide a smell sensing element which is capable of accurately and speedily measuring various types of smells and also to provide a portable and inexpensive smell sensing device using the element.

In order to accomplish the above object, a smell sensing element according to the present invention comprises a semiconductor portion formed mainly of $SnO_2$.

To the semiconductor portion is added a first component of at least one selected from the group consisting of oxides of alkaline earth metals and with a second component of at least one selected from the group consisting of oxides of Sc, Y, Ti, Zr, Hf, Th, Al, Ga and lanthanoids.

Functions and effects of this smell sensing element will be described next.

In general, the smell is attributable to a volatile vapor of alcohols, acetylene, hydrogen sulfide, methyl mercaptan, trimethylamine, styrene, esters, aldehydes, ketones of carboxylic acids, and others. Of these volatile vapors, the smell intensity of gases (vapors) acting on the sensory membrane of olfactory cells tends to be enhanced when the degree of unsaturation of the hydrocarbons is larger; and the smell intensity of triply unsaturated hydrocarbons is higher than that of doubly unsaturated ones, and the intensity tends to increase with increase in the number of the doubly unsaturated bonds in the hydrocarbons. In the element of the present invention, the aforementioned first and second components are added to the semiconductor portion. As illustrated by some examples tabulated in Tables 1, 2 and 3 shown in FIG. 4, the element gives a higher selectively to smelling gases than to less-smelling ones such as $H_2$, CO, $C_4H_{10}$ or the like. Further, FIG. 5(a) and FIG. 5(b) show the initial response profiles for ethanol vapor (100 ppm) of this smell sensing element. The response of the element to which $C_2O$ alone was added as the first component (FIG. 5(a)), was unstable during a certain initial period of operation. On the other hand, the element to which both $C_aO$ as the first component and $L_aO$ 3/2 as the second component (FIG. 5(b)) were added, provided a stable sensitivity to the ethanol vapor (100 ppm) from the beginning. That is, the element to which the first and second components are added is supposed to be able to sense smelling gases speedily and accurately.

According to the above-described smell sensing element of the present invention, an accurate evaluation may be made speedily without erroneous sensing of smell-less gases; and then it becomes possible to evaluate smell intensity easily in real time without requiring much experience. Consequently, the smell sensing element may readily serve for evaluation of freshness or ripeness of foods and also for evaluation of olfactory medical diagnosis which has so far depended on the expertise and experience of a medical doctor.

Further, a smell sensing device can be constituted by the above-described smell sensing element and a readout means.

This smell sensing device is capable of measuring various types of smells in an accurate and speedy manner, and the device may be formed to be compact, portable and inexpensive.

BRIEF DESCRIPTION OF THE DRAWINGS

Accompanying drawings FIGS., 1 through 5, illustrate one preferred embodiment of a smell sensing element and a smell sensing device utilizing the element related to the present invention; in which.

DESCRIPTION OF PREFERRED EMBODIMENT

One preferred embodiment of a smell sensing device related to the present invention will be particularly described hereinafter with reference to the accompanying drawings.

Figure 1:
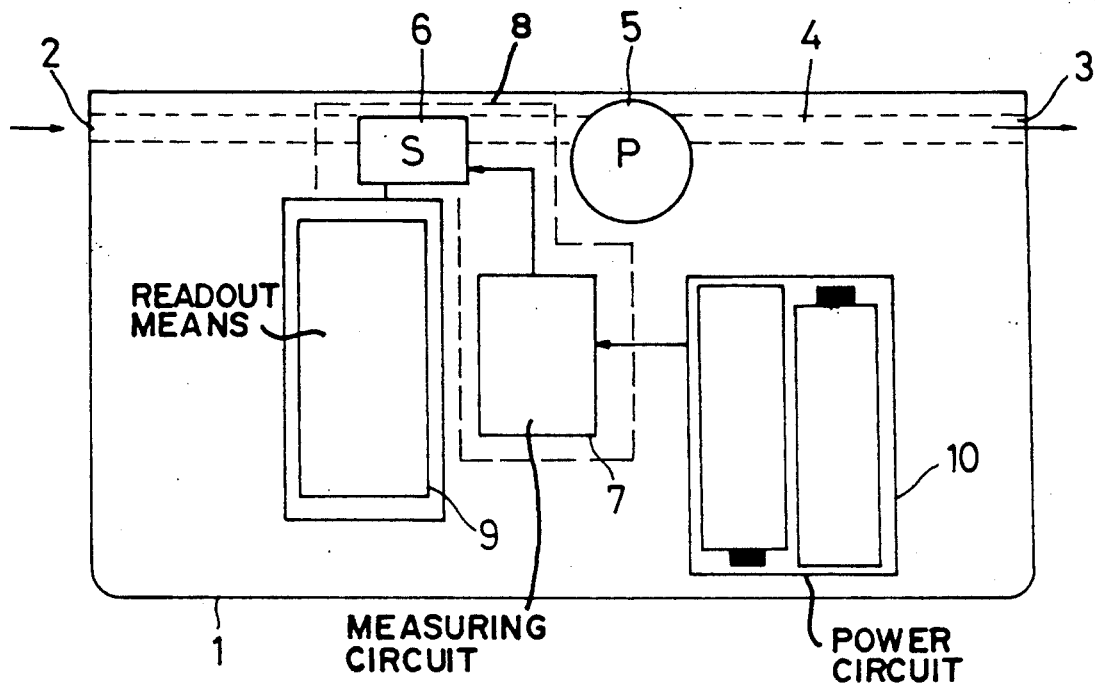
FIG. 1 is a schematic view showing the construction of the smell sensing device.
Figure 2:
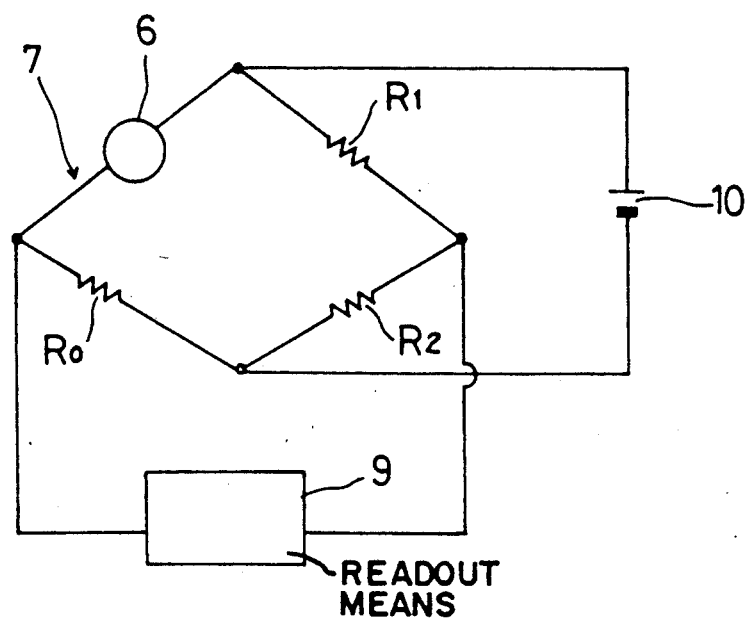
FIG. 2 is a circuit diagram of the smell sensing device of FIG. 1.

FIG. 1 is a schematic view showing the construction of the smell sensing device of the invention. Reference numeral 1 denotes a casing including an inlet opening 2, an outlet opening 3 and a passage 4 formed between the openings 2 and 3. Numeral 5 denotes a suction pump. Numeral 6 denotes a semiconductor type smell sensing element disposed in the passage 4 so as to be exposed to a smell introduced through the inlet opening 2. Numeral 7 denotes a measuring circuit constructed as e.g. a bridge circuit shown in FIG. 2, the measuring circuit 7 constituting a smell sensing unit 8 together with the sensing element 6. Numeral 9 denotes a readout means constituted by e.g. a voltmeter and operable to provide digital or analog readout values representative of a smell intensity. Numeral 10 denotes a power source incorporating e.g. a rectifier circuit for obtaining an appropriate direct current voltage from a battery or from a commercial power source.

Further, reference characters R0, R1 and R2 denote resistances. The temperature of the smell sensing element 6 are controlled through a bridge voltage from the power source 10.

Incidentally, the conductivity of the $SnO_2$ semiconductor may be controlled by doping the same with an appropriate amount of $Sb^{5+}$, $Nb^{5+}$ or the like.

It is also to be noted that the present invention may be applied also to a batchwise smell sensing device without the suction pump 5 in place of the suction flow type smell sensing device shown in FIG. 1.

Further, the smell sensing unit 8 and the smell readout means 9 may be formed as separate units instead of placing the same close to each other. Also, it is conceivable to provide the smell readout means 9 with a peak-hold or other indicators such as a buzzer and a lamp.

Figure 3A:
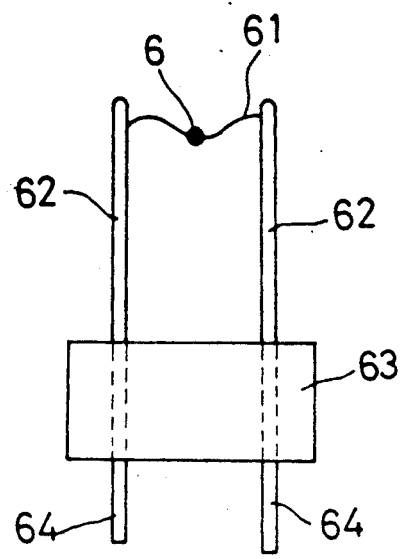
FIG. 3(a) shows a support mechanism for the smell sensing element.

FIG. 3(a) shows one example of a support mechanism for the smell sensing element 6 used in the embodiment shown in FIG. 1. In this FIG. 3(a), the smell sensing element 6 is attached to a support pins 62 via a heater cable 61. Numeral 63 denotes a socket and numerals 64 denote a power terminal.

Figure 3B:
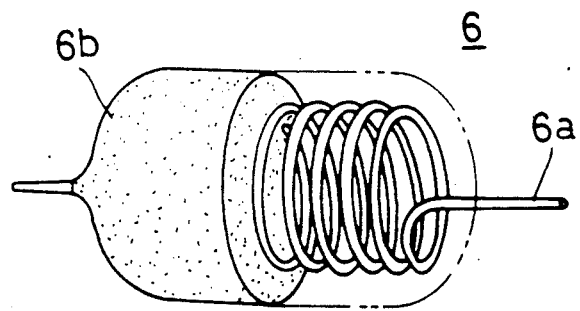
FIG. 3(b) is a partially cutaway perspective view showing a sintered spherical type smell sensing element.

FIG. 3(b) shows the smell sensing element 6 formed as a sintered bead type. This element is constituted by a platinum coil 6a coated with a sintered semiconductor 6b formed by adding to the sintered $SnO_2$ semiconductor 0.25 to 20 mol % of a first component of at least one selected from the group consisting of oxides of alkaline earth metals and also 0.25 to 20 mol % of a second component of at least one selected from the group consisting of oxides of Sc, Y, Ti, Zr, Hf, Th, Al, Ga and lanthanoids (the mixture ratio of the first component relative to the second component being limited below 90%).

Figure 3C:
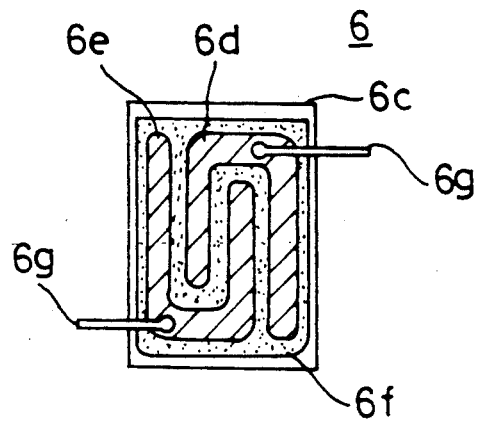
FIG. 3(c) is a cross sectional view showing a substrate type smell sensing element, FIG. 4 graphically shows measurements of various types of gases obtained by the smell sensing element.

FIG. 3(c) shows the smell sensing element 6 using a substrate constituted by electrodes 6d and 6e formed thereon, the platinum cable 6g attached to each electrode (6d and 6e), and a sintered thick film of semiconductor portion 6f covered thereon. The sintered thick film composed of the $SnO_2$ semiconductor is added with 0.25 to 20 mol % of the first component of at least one selected from the group consisting of oxides of alkaline earth metals and with 0.25 to 20 mol % of the second component of at least one selected from the group consisting of oxides of Sc, Y, Ti, Zr, Hf, Th, Al, Ga and lanthanoids. The mixing ratios of the first component to the second component contained in the semiconductor portion 6f are limited to no greater than 90%.

Figure 5A:
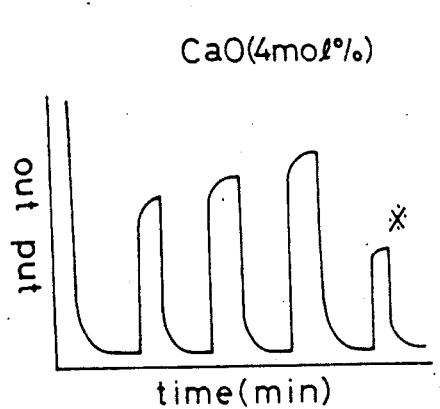
FIG. 5(a) is a graph showing measured initial response profiles of the smell sensing element to which $C_aO$ alone has been added.
Figure 5B:
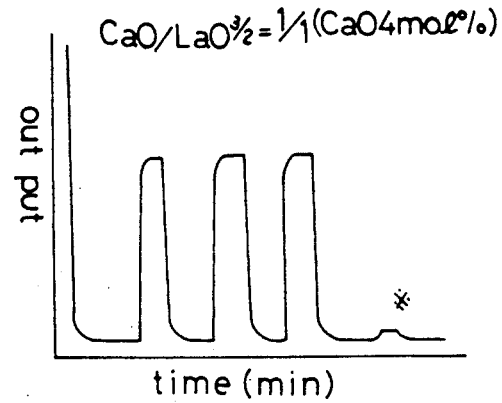
FIG. 5(b) is a graph showing the initial response profiles obtained for the smell sensing element to which $C_aO$ and $L_aO$ 3/2 has been added.

This smell sensing element 6, as tabulated in Tables 1, 2 and 3, had a high smell selectivity: the element had high sensitivities to smelling gases, while low sensitivities to smell-less gases, such as $H_2$, CO, $C_4H_{10}$ or like. Further, as shown in FIG. 5(b), the sensing element 6 achieved quicker response and more stable sensitivity and further gave low sensitivity to $H_2$ (1000 ppm) denoted by an asterisk when the same is added with both of the first and second components rather than only the first component.

Especially in the case of an addition with CaO—$LaO_{3/2}$ group, as tabulated in Table 2, the sensitivity to ethanol (100 ppm) reached its maximum around equimolecular quantities of two components. At the same time, the sensitivity ratios of ethanol to $H_2$, CO, $C_4H_{10}$ or the like reached its maximum.

Figure 4:
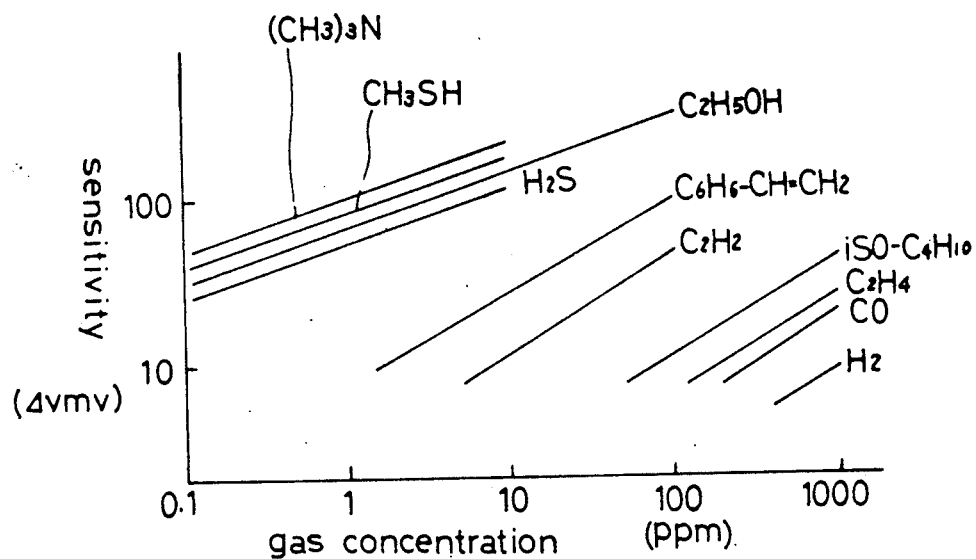

FIG. 4 shows logarithmically linear relationships between sensitivity (▲VnV) and gas concentration (ppm), that is, their various power relationships.

Incidentally, the relative smell intensities among smelling gases tend to increase with increase in the degree of unsaturation (i.e. double, triple bonds or the number) in hydrocarbons. The organic molecules with the atoms of O, H and S tend to have a smell. In view of these facts, the smell sensing element 6 of the present invention has the following characteristics:

1. Its sensitivities to hydrocarbons increases with increase in the degree of unsaturation.
2. The element is more sensitive to the triply unsaturated hydrocarbons than to the doubly unsaturated ones.
3. The element has high sensitivities to hydrocarbons containing O, N, S or the like; and
4. The smelling gases have reducibility which is a requirement for the element to be sensible.

It is suggested that such molecular characteristics of gases sensitive to this element is similar to those of smelling gases and is capable of using as an alternative measurements of smell intensity.

The manufacturing processes of such a smell sensing element 6 will be briefly described as follows:

(1) The powder of $SnO_2$ semiconductor was obtained by pyrolysis of the hydrolysis products provided from $SnCl_4$-aqueous solution added with a small amount of $SbCl_5$ to obtain an appropriate conductivity. The powder of the $Sb^{5+}$-dopped and $SnO_2$ was applied onto a platinum coil 1 to form a bead of ca. 0.4 mm diameter. After drying, the bead was heated by allowing a given electric current flow through the platinum coil 1 and the $SnO_2$ powder was sintered for one hour at a given temperature, e.g. about 650 degrees Celsius. The bead of the $SnO_2$ semiconductor thus obtained has a porous structure favorable for obtaining a high sensitivity.

(2) The porous bead of $SnO_2$ semiconductor was then impregnated with an aqueous solution added with the first component of at least one nitrate of alkaline earth elements (Be, Mg, Ca, Sr, Ba) and with the second component of at least one oxide of nitrates of Sc, Y, Zr, Hf, Th, Al, Ga and lanthanoides (La, Ce, Pr, Tb, Yb, etc.) and $TiCl_3$. Then, the semiconductor is again dried in the same manner as the above process (1). Their salts supported in the porous semiconductor were decomposed into their oxides in air at the temperature of ca. 600 degrees Celsius by Joule heat of the platinum coil 1.

The smell sensing element 6 obtained through the above-described processes (1) and (2) was incorporated into a conventional bridge circuit.

The temperature of the smell sensing element was ca. 400 degrees Celsius by joule heat of the coil 1 controlled by a bridge voltage source 10.

Instead of the above-described impregnation method, other conventional methods, such as the coprecipitation method or the electrophoresis method, may be employed.

Each amount of the first and second components added to the element 6 should preferably range from 0.25 to 20 mol %, respectively, for the proper operation. That is, if either of their contents is below the lower limit of 0.25 mol %, there occurs deterioration in the selectivity or the stability of the element. On the other hand, if either of their contents exceeds the defined upper limit of 20 mol %, there occurs disadvantageous reduction in the sensitivities to the various gases.

The functions of the smell sensing device shown in FIG. 1 are as follows:

First, the device draws in smelling air from the ambient surroundings at a flow rate of ca. 500 ml/min. by the suction pump 5. The resistance of the element 6 decreases in proportion to the concentration of smelling gases in the presence of the introduced smelling air, and the corresponding sensor output of the bridge circuit 7 is displayed on the readout means 9.

Note: In the following Tables 1 through 3, the reference letters 'A' through 'J' respectively denote: 'A' for trimethylamine, 'B' for methyl sulfide, 'C' for hydrogen sulfide, 'D' for ethanol, 'E' for styrene, 'F' for acetylene, 'G' for isobutane, 'H' for ethylene, 'I' for hydrogen and 'J' for carbon monoxide.

TABLE 1-a

Dependence of sensitivities to various sample gases on additives

| additives (mole ratios) in the presence of CaO (4 mol %) | | sensitivities (mV) to sample gases | | |
|---|---|---|---|---|
| | | A 10 ppm | B 10 ppm | C 10 ppm |
| $CaO/Al_2O_3 =$ | 1/0.5 | 135 | 110 | 71 |
| $CaO/Al_2O_3 =$ | 1/1 | 150 | 130 | 85 |
| $CaO/GaO_{3/2} =$ | 1/0.5 | 138 | 112 | 70 |
| $CaO/GaO_{3/2} =$ | 1/1 | 155 | 125 | 80 |
| $CaO/ZrO_2 =$ | 1/0.5 | 90 | 73 | 43 |
| $CaO/ZrO_2 =$ | 1/1 | 108 | 88 | 52 |
| $CaO/YO_{3/3} =$ | 1/0.5 | 150 | 122 | 71 |
| $CaO/YO_{3/2} =$ | 1/1 | 110 | 91 | 51 |
| $CaO/LaO_{3/2} =$ | 1/0.5 | 170 | 138 | 90 |

TABLE 1-a-continued

Dependence of sensitivities to various sample gases on additives

| additives (mole ratios) in the presence of CaO (4 mol %) | | sensitivities (mV) to sample gases | | |
|---|---|---|---|---|
| | | A 10 ppm | B 10 ppm | C 10 ppm |
| $CaO/PrO_2 =$ | 1/1 | 155 | 125 | 70 |
| $CaO/YbO_2 =$ | 1/1 | 148 | 119 | 71 |
| $CaO/ScO_{3/2} =$ | 1/1 | 115 | 95 | 60 |
| $CaO/TiO_2 =$ | 1/1 | 100 | 83 | 48 |
| $CaO/ThO_2 =$ | 1/1 | 112 | 89 | 52 |
| $MgO/LaO_{3/2} =$ | 1/1 | 81 | 60 | 40 |

TABLE 1-b

Dependence of sensitivities to various sample gases on additives

| additives (mole ratios) in the presence of CaO (4 mol %) | | sensitivities to sample gases (mV) | | | | | |
|---|---|---|---|---|---|---|---|
| | | D 100 (ppm) | E 100 (ppm) | F 100 (ppm) | G 1000 (ppm) | H 1000 (ppm) | I 1000 (ppm) |
| $CaO/Al_2O_3 =$ | 1/0.5 | 175 | 41 | 54 | 29 | 20 | 21 |
| $CaO/Al_2O_3 =$ | 1/1 | 210 | 61 | 70 | 33 | 25 | 30 |
| $CaO/Ga_{3/2} =$ | 1/0.5 | 178 | 46 | 89 | 34 | 20 | 26 |
| $CaO/GaO_{3/2} =$ | 1/1 | 200 | 52 | 100 | 40 | 25 | 35 |
| $CaO/ZrO_2 =$ | 1/0.5 | 117 | 35 | 36 | 29 | 17 | 22 |
| $CaO/ZrO_2 =$ | 1/1 | 140 | 40 | 44 | 36 | 21 | 26 |
| $CaO/YO_{3/2} =$ | 1/0.5 | 194 | 47 | 49 | 32 | 25 | 27 |
| $CaO/YO_{3/2} =$ | 1/1 | 142 | 44 | 36 | 30 | 19 | 17 |
| $CaO/LaO_{3/2} =$ | 1/0.5 | 220 | 46 | 42 | 27 | 19 | 8 |
| $CaO/PrO_2 =$ | 1/1 | 200 | 42 | 40 | 37 | 15 | 9 |
| $CaO/YbO_2 =$ | 1/1 | 190 | 40 | 50 | 35 | 16 | 9 |
| $CaO/ScO_{3/2} =$ | 1/1 | 150 | 40 | 35 | 29 | 20 | 21 |
| $CaO/TiO_2 =$ | 1/1 | 130 | 45 | 50 | 40 | 25 | 22 |
| $CaO/ThO_2 =$ | 1/1 | 145 | 42 | 46 | 40 | 24 | 30 |
| $MgO/LaO_{3/2} =$ | 1/1 | 110 | 30 | 25 | 12 | 10 | 5 |

TABLE 2

Dependence of sensitivities (mV) to various gases on CaO contents in $CaO.LaO_{3/2}$ (CaO content fixed at 4 mol % to $SnO_2$)

| sample gases | CaO contents (mol %) in $CaO.LaO_{3/2}$ | | | | | |
|---|---|---|---|---|---|---|
| | 100 | 80 | 67 | 50 | 33 | 20 |
| A 10 ppm | 47 | 130 | 170 | 220 | 204 | 173 |
| B 10 ppm | 37 | 106 | 138 | 180 | 163 | 125 |
| C 10 ppm | 23 | 65 | 90 | 114 | 100 | 88 |
| D 10 ppm | 28 | 82 | 110 | 147 | 134 | 115 |
| G 1000 ppm | 8 | 21 | 27 | 44 | 34 | 20 |
| I 1000 ppm | 4 | 6 | 8 | 9 | 6 | 2 |
| J 1000 ppm | 5 | 11 | 18 | 20 | 22 | 8 |

TABLE 3

Dependence of sensitivities (mV) to various sample gases on CaO contents (mol %) to $SnO_2$ in equimolar mixture of $CaO.LaO_{3/2}$

| sample gases | CaO contents (mol %) to $SnO_2$ | | | | | | | | |
|---|---|---|---|---|---|---|---|---|---|
| | 0.13 | 0.25 | 0.5 | 1 | 2 | 4 | 8 | 12 | 16 | 20 |
| A 10 ppm | 210 | 224 | 230 | 248 | 242 | 220 | 190 | 125 | 69 | 27 |
| B 10 ppm | 174 | 185 | 195 | 200 | 198 | 180 | 157 | 102 | 50 | 22 |
| C 10 ppm | 110 | 115 | 123 | 130 | 125 | 114 | 100 | 66 | 35 | 13 |
| D 10 ppm | 130 | 150 | 159 | 165 | 160 | 147 | 139 | 83 | 46 | 21 |
| G 1000 ppm | 135 | 125 | 102 | 82 | 60 | 44 | 36 | 15 | 10 | 4 |
| I 1000 ppm | 61 | 40 | 32 | 18 | 11 | 9 | 7 | 5 | 3 | 2 |
| J 1000 ppm | 206 | 78 | 35 | 31 | 26 | 20 | 20 | 21 | 12 | 8 |

What is claimed is:

1. A smell sensing element of a smell sensing device for sensing the presence of an odorous gas by changing its resistance value through adsorption of said gas, comprising:

a semiconductor portion comprised primarily of $SnO_2$ and said first and second components carried by said $SnO_2$ wherein said first component is of at least one selected from the group consisting of oxides of alkaline earth metals; and said second component is of at least one selected from the group consisting of oxides of Sc, Y, Ti, Zr, Hf, Th, Al, Ga and lanthanoids.

2. A smell sensing element as claimed in claim 1 wherein said first and second components exist in said semiconductor in a mixed state.

3. A smell sensing element as claimed in claim 1, wherein with said first and said second components exist in said semiconductor in the range of 0.25 to 20 mol %.

4. A smell sensing element as claimed in claim 2, wherein said first and said second components exist in said semiconductor in the range of 0.25 to 20 mol %.

5. A smell sensing device including a smell sensing element and readout means for displaying an output of the smell sensing element, the smell sensing element sensing the presence of an odorous gas by changing its resistance value through absorption of said gas, said smell sensing element comprising:

a semiconductor portion comprised primarily of $SnO_2$ and said first and second components carried by said $SnO_2$ wherein said first component is of at least one selected from the group consisting of oxides of alkaline earth metals; and said second component is of at least one selected from the group consisting of oxides of Sc, Y, Ti, Zr, Hf, Th, Al, Ga and lanthanoids.

6. A smell sensing device as claimed in claim 1, wherein said first and second components exist in said semiconductor in a mixed state.

7. A smell sensing device as claimed in claim 5, wherein said first and said second components exist in said semiconductor in the range of 0.25 to 20 mol %.

8. A smell sensing device as claimed in claim 5, wherein said first and second components exist in said semiconductor portion in an impregnated state.

9. A smell sensing device as claimed in claim 6, wherein said first and said second components exist in said semiconductor in the range of 0.25 to 20 mol %.

10. A smell sensing device as claimed in claim 6, wherein said first and second components exist in said semiconductor portion in an impregnated state.

11. A smell sensing device, comprising:

a power source;

a casing having an inlet opening and an outlet opening and a passage extending between the openings;

a smell sensing element disposed in said passage for sensing the presence of an odorous gas by changing its resistance value through absorption of said gas; and readout means for displaying an output of the smell sensing element, said smell sensing element comprising:

a conductor portion and a semiconductor portion comprised primarily of $SnO_2$ and said first and second components carried by said $SnO_2$ wherein said first component is of at least one selected from the group consisting of oxides of alkaline earth metals; and said second component is of at least one selected from the group consisting of oxides of Sc, Y, Ti, Zr, Hf, Th, Al, Ga and lanthanoids.

* * * * *